United States Patent [19]

Chenard

[11] Patent Number: 5,696,126
[45] Date of Patent: Dec. 9, 1997

[54] PRODRUG ESTERS OF PHENOLIC 2-PIPERIDINO-1-ALKANOLS

[75] Inventor: Bertrand Leo Chenard, Waterford, Conn.

[73] Assignee: Pfizer Inc., New York, N.Y.

[21] Appl. No.: 418,718

[22] Filed: Apr. 7, 1995

Related U.S. Application Data

[62] Division of Ser. No. 119,122, Sep. 16, 1993, Pat. No. 5,455,250, which is a continuation of Ser. No. 687,273, Apr. 18, 1991, abandoned.

[51] Int. Cl.$^6$ .............. A61K 31/445; C07D 211/44; C07D 211/14
[52] U.S. Cl. .............. 514/278; 514/327; 546/16; 546/216; 546/217
[58] Field of Search ............ 546/216, 217, 546/16; 514/327, 278

[56] References Cited

U.S. PATENT DOCUMENTS

| | | | |
|---|---|---|---|
| 4,690,931 | 9/1987 | Wick et al. | 514/317 |
| 5,185,343 | 2/1993 | Chenard | 514/278 |
| 5,272,160 | 12/1993 | Chenard | 514/327 |
| 5,338,754 | 8/1994 | Chenard | 514/422 |
| 5,391,742 | 2/1995 | Chenard | 546/14 |

FOREIGN PATENT DOCUMENTS

| | | |
|---|---|---|
| 0441506 | 8/1991 | European Pat. Off. . |
| WO9014087 | 11/1990 | WIPO . |
| WO9014088 | 11/1990 | WIPO . |
| WO91/17156 | 11/1991 | WIPO . |

OTHER PUBLICATIONS

Chemical Abstracts vol.99,No.17,abst.no.139,786y,Oct.24, 1983.
Chemical Abstracts,vol.101,No.23,abst.no.210,992e,Dec.3, 1984.

*Primary Examiner*—Alan L. Rotman
*Attorney, Agent, or Firm*—Peter C. Richardson; Gregg C. Benson; Robert T. Ronau

[57] ABSTRACT

Phenolic prodrug esters of certain 1-(hydroxyphenyl)-2-piperidino-1-alkanol derivatives, which are useful in the treatment of stroke, traumatic head injury and CNS degenerative disease; and intermediates useful in their synthesis.

7 Claims, No Drawings

PRODRUG ESTERS OF PHENOLIC 2-PIPERIDINO-1-ALKANOLS

This is a division of application Ser. No. 08/119,122, filed on Sep. 16, 1993, now U.S. Pat. No. 5,455,250 which is a continuation PCT/U.S.92/02131, filed Mar. 24, 1992, which is a continuation of application Ser. No. 07/687,273, filed Apr. 18, 1991 (now abandoned).

The present invention is directed to prodrug esters of phenolic 2-piperidino-1-alkanols, as depicted by the formulas (I) and (II), below; to pharmaceutical compositions thereof; to a method of treating stroke, traumatic head injury, or a CNS degenerative disease therewith; and to ketone intermediates of the formulas (III) and (IV), below, which are useful in their synthesis.

The phenolic compounds from which the present compounds derive are disclosed in my International Applications Published Under the Patent Cooperation Treaty, International Publication Nos. WO 90/14087 and (now U.S. Pat. No. 5,185,343, issued Feb. 9, 1993) both published on Nov. 29, 1990, and hereby incorporated by reference. These phenolic compounds are of the formulas

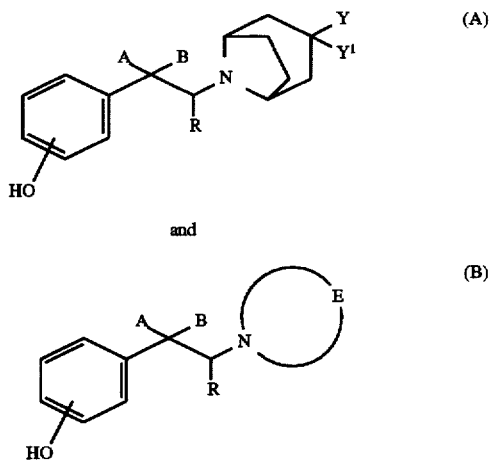

wherein A and B are taken separately and A is hydrogen and B is hydroxy, or A and B are taken together and are oxygen (forming a carbonyl group); and the groups R, E, Y and $Y^1$ are as defined below for the corresponding ester derivatives of the formulas (I), (II), (III) and (IV).

The compounds of the formulas (A) and (B) wherein the groups A and B are taken separately to form a 1-alkanol, like the present compounds of the formulas (I) and (II), generally possess selective antiischemic and excitatory amino acid receptor blocking activity (i.e., a neuroprotective effect) in good measure, while at the same time they have lowered or no significant hypotensive effect.

Ifenprodil, a racemic, so-called dl-erythro compound having the relative stereochemical formula

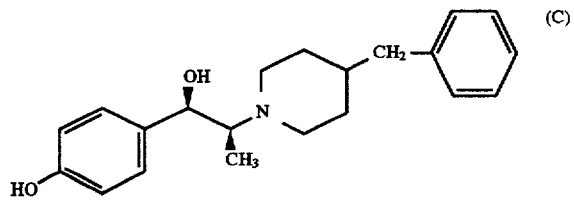

has been shown to possess antiischemic and excitory aminoacid receptor blocking activity; Gotti et al., J. Pharm. Exp. Therap., v. 247, pp. 3211–21 (1988); Carter et al., loc. cit., pp. 1222–32 (1988). See also French Patent 2546166.

However, in ifenprodil, this activity is not selective. Indeed ifenprodil is marketed as a hypotensive agent, a utility shared by a number of close analogs; Carron et al., U.S. Pat. No. 3,509,164; Carron et al., Drug Res., v. 21, pp. 1992–1999 (1971).

So-called prodrug esters, which in general enhance oral absorption and are hydrolyzed in vivo to form the active component of the ester, have become quite common in the medicinal art. For example, Bundgaard et al., J. Med. Chem., v. 32, pp. 2503–7 (1989) have described certain prodrug esters of the type

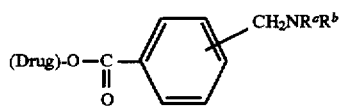

wherein $R^a$ and $R^b$ are taken separately, $R^a$ is hydrogen or lower alkyl, and $R^b$ is lower alkyl; or $R^a$ and $R^b$ are taken together with the nitrogen to which they are attached to form, for example, a morpholine or 4-methylpiperazine ring.

The present invention is directed to so-called pro-drug esters of the formulas

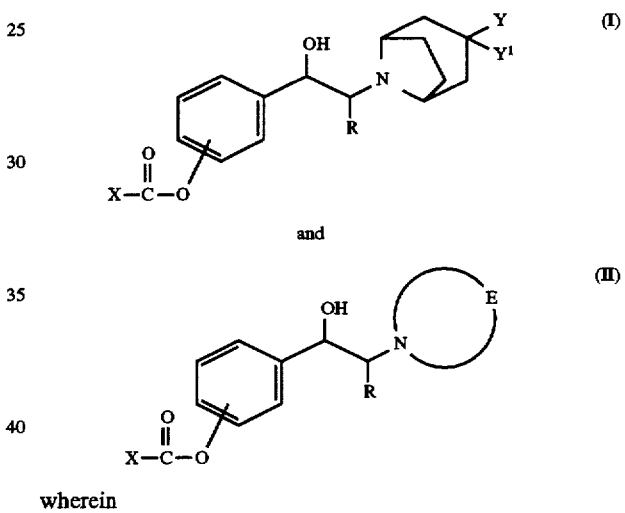

wherein
E is

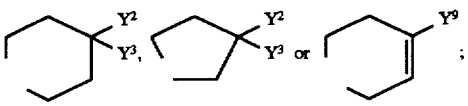

R is H, $(C_1-C_6)$alkyl, $(C_2-C_6)$alkenyl or $(C_2-C_6)$alkynyl;
X is phenyl, benzyl, $(C_1-C_3)$alkoxy, phenoxy or one of said groups substituted on aromatic carbon by

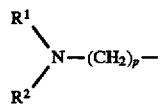

p is 1 or 2;
$R^1$ and $R^2$ are taken separately and are each independently hydrogen or $(C_1-C_6)$alkyl, or $R^1$ and $R^2$ are taken together with the nitrogen to which they are attached to form a pyrrolidine, piperidine or morpholine ring, or one of said rings substituted by $(C_1-C_3)$alkyl;
when either Y and $Y^1$ or $Y^2$ and $Y^3$ are taken together, they are

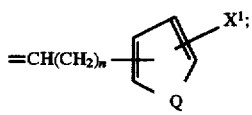

or when Y and Y¹ are taken separately, Y is hydrogen or OH, and Y¹ is

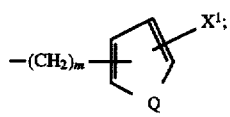

or

Y is hydrogen and Y¹ is

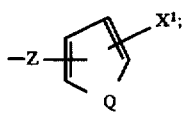

when Y² and Y³ are taken separately, and Y² is OH and Y³ is

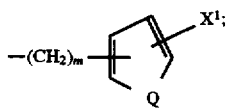

Y⁹ is

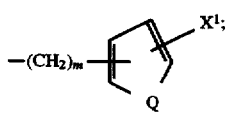

n is 0, 1, 2 or 3;

m is 0, 1, 2, 3 or 4;

Q is S or CH=CH;

X¹ is hydrogen, $(C_1-C_3)$alkyl, $(C_1-C_3)$alkoxy or halo; and

Z is O, S, SO or $SO_2$; or a pharmaceutically-acceptable acid addition salt thereof.

Said acid addition salts include, but are not limited to, those formed with such acids as HCl, $H_2SO_4$, $H_3PO_4$, $HNO_3$, $CH_3SO_3H$, $pCH_3C_6H_4SO_3H$, acetic acid, maleic acid and citric acid.

The preferred compounds are racemic or optically active compounds wherein R is methyl and have 1S*,2S* relative stereochemistry:

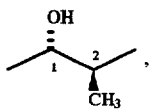

alternatively and equivalently depicted as:

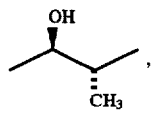

and referred to as 1R,2R*, relative stereochemistry. See Rigaudy et al., eds., IUPAC Nomenclature of Organic Chemistry, 1979 Edition, Pergamon Press, New York, 1979, p. 482. Preferred values of X are phenyl, p-(dimethylaminomethyl)phenyl, p-(diethylaminomethyl)phenyl, m-(diethylaminomethylphenyl, p-(piperidinomethyl)phenyl, p-(2-methylpiperidinomethyl)phenyl and p-(morpholinomethyl)phenyl. The preferred position of the XCOO group on the benzene ring is para to the 1-hydroxyalkyl substituent.

The present invention is further directed to pharmaceutical compositions comprising a neuroprotective amount of a compound of formula (I) or (II) and to a method of treating stroke, traumatic head injury or a CNS degenerative disease in man which comprises treatment with a neuroprotective amount of one of said compounds. Said compositions and treatment method include not only the oral route of administration, where absorption from the intestinal tract is generally enhanced, but also parenteral routes of administration (e.g., intravenous, intramuscular). The present, intact prodrug esters also generally cross the blood-brain barrier, and further, are capable of hydrolysis in brain tissue once across that barrier. Thus parenteral (as well as oral) administration of these esters can lead to desirable enhancement of active drug levels in the brain.

The present invention is also directed to ketone precursors of the present 1-alkanol derivatives, of the formulas

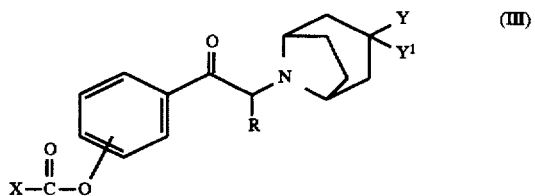

and

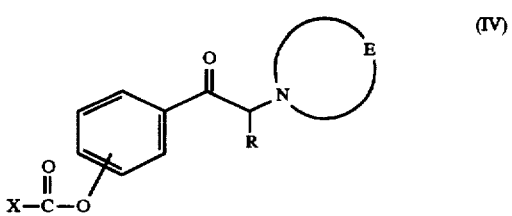

wherein

E, R, X, Y and Y¹ are as defined above.

It will be noted that those compounds of the formulas (I) and (II), which are 1-alkanols, possess an asymmetric C-1 carbon, while those wherein R is other than hydrogen possess a second asymmetric center at the C-2 carbon of the alkanol. Similarly, in those compounds of the formulas (III) and (IV) which are 1-alkanones wherein R is other than hydrogen possess a C-2 asymmetric carbon. It will be evident to those skilled in the art of organic chemistry, therefore, that such compounds can be resolved into optical isomers showing equal but opposite rotation of plane polarized light. For example, all of these compounds are potentially resolved by fractional crystallization of their diastereomeric acid addition salts formed with an optically active acid; while the alcohols are also potentially resolved by chromatography or fractional crystallization of esters derived by reaction with activated forms of optically active acids or with optically active isocyanates. Thus, the present invention should not be construed as limited to the racemic forms of the present compounds.

The present invention is readily carried out. According to the preferred route, the compounds of the above formula (I) and (II) are formed by conventional hydride reduction of a corresponding, already acylated ketone of the above formula (III) or (IV). Hydride reducing agents generally useful in this reduction include lithium aluminum hydride and sodium borohydride. Generally an excess of the hydride reducing agent employed, but to avoid reduction of the ester group, lithium aluminum hydride is employed at low temperature, e.g., at –50° C. to –100° C., conveniently about –78° C., the temperature of a dry ice-acetone bath. In any event, the hydride reduction is carried out in a reaction-inert solvent, such as tetrahydrofuran in the case of lithium aluminum hydride and absolute ethanol in the case of sodium borohydride. With sodium borohydride temperature is less critical, with temperatures in the range of 0°–30° C. being generally preferred.

As used in the preceding paragraph, and elsewhere herein, the expression "reaction inert solvent" refers to any solvent which does not interact with starting materials, reagents, intermediates or products in a manner which adversely affects the yield of the desired product.

Further according to the preferred method of preparing the present compounds of the above formulas (I) and (II), the acylated ketone precursors of the above formulas (III) and (IV) are obtained by acylation of a known ketone derivative, respectively, of the formulas (A) and (B), above, wherein A and B are taken together to form a carbonyl group. Said acylation is readily accomplished by a number of conventional methods which are well known in the organic chemical art. When the ketone (A) or (B) contains a tertiary aliphatic alcohol group (which is the case when either Y or $Y^2$ is hydroxy), this acylation is necessarily selective, but still, in general, is readily accomplished because of the greater activity of the phenolic group relative to the hindered tertiary, alcoholic group. The preferred methods borrow from coupling methods used in the synthesis of peptides. According to one of the preferred methods, a substantially molar equivalent of the acid is coupled with the phenolic ketone by the action of substantially one molar equivalent of 1-ethyl-3-(3-dimethylaminopropyl)carbodiimide. This coupling is generally carried out in a reaction-inert solvent such as methylene chloride in the presence of 10–20% molar excess of a tertiary amine such as 4-dimethylaminopyridine. Temperature is not critical, with temperatures in the range of 0°–50° C. being generally satisfactory, and ambient temperatures (generally about 17°–27° C.) preferred, since the cost of heating or cooling is avoided.

Alternatively, the compounds of the formulas (I) and (II) are obtained directly by acylation of the appropriate, known phenolic 1-alkanol compound of the above formulas (A) and (B) wherein A and B are taken separately, A is hydrogen and B is hydroxy. Indeed, when the 1-alkanol is already available in resolved form, this is a preferred route to the optically active forms of the present esters.

The ketonic and 1-alkanol precursors of the formulas (A) and (B) depicted above are disclosed in my Published International Patent Application Number WO 90/14087 cited above. In the ketones of that reference wherein the phenol group is protected, the protecting group is removed by the same methods there particularly disclosed for the deprotection of phenol-protected 1-alkanol derivatives. Such a deprotection method is also specifically described in Preparations detailed below.

The inherent antiischemic activity and ability of the present prodrug esters to block excitatory amino acid receptors is reflected from the study of the corresponding phenolic 1-alkanol compounds (of the above formulas (A) and (B) wherein A and B are taken separately, A is hydrogen and B is hydroxy). These biological methods are detailed in the prior art references cited above, viz, Gotti et al., Carter et al. and my published International application WO 90/14088 (now U.S. Pat. No. 5,185,343, issued Feb. 9, 1993).

The present prodrug esters are dosed at weight levels which are chemically equivalent to the weight levels of the fully active phenolic forms, as detailed in my published International application WO 90/14088 (now U.S. Pat. No. 5,185,343, issued Feb. 9, 1993) cited above. For example, for a 10 mg dose of a phenol having a molecular weight of 327, the amount of a prodrug ester having a molecular weight of 516 will be $$10 \text{ mg} \times \frac{516}{327} = 15.8 \text{ mg}$$

The present prodrug esters are formulated into oral and parenteral dosage forms according to the same conventional methods which are used in the formulation of the corresponding phenols as described in my published International application WO 90/14088 (now U.S. Pat. No. 5,185,343, issued Feb. 9, 1993).

The present invention is illustrated by the following examples, but is not limited to the details thereof.

All non-aqueous reactions were run under nitrogen for convenience and generally to maximize yields. All solvents/diluents were dried according to standard published procedures or purchased in a predried form. All reactions were stirred either magnetically or mechanically. NMR specta are recorded at 300 MHz-and are reported in ppm. The NMR solvent was $CDCl_3$ unless other specified.

EXAMPLE 1

2-(4-Hydroxy-4-phenylpiperidino)-1-(4-(4-(morpholinomethyl)benzoyloxy)phenyl)-1-propanone To a mixture of 4-(morpholinomethyl)benzoic acid (3.17 g, 12.3 mmol), 1-(4-hydroxyphenyl)-2-(4-hydroxy-4-phenylpiperidino)-1-propanone (4.0 g, 12.29 mmol), and 1-ethyl-3-(3-dimethylaminopropyl)-carbodiimide hydrochloride (2.36 g, 12.31 mmol) in methylene chloride (75 mL) was added 4-dimethylaminopyridine (1.88 g, 15.39 mmol). The heterogeneous mixture was allowed to stir overnight under a nitrogen atmosphere at ambient temperature. The mixture was washed with saturated aqueous bicarbonate (2×50 mL), dried by filtration through phase separating filter paper, and concentrated to a glassy yellow solid. Trituration with ether and hexane yielded 5.17 g, 80% of a light yellow solid product which was suitable for further reaction without additional purification. A sample recrystallized from ethyl acetate/hexane had: m.p. 126°–126.5° C.; NMR ($CDCl_3$) 8.22 (d, J=8.6 Hz, 2 H), 8.13 (d, J=7.8 Hz, 2 H), 7.47 (t, J=7.3 Hz, 4 H), 7.34–7.19 (m, 5 H), 4.13 (q, J=6.6 Hz, 1 H), 3.70 (t, J=4.4 Hz, 4 H), 3.57 (s, 2 H), 2.97–2.79 (m, 2 H), 2.67–2.60 (m, 2 H), 2.44 (t, J=4.5 Hz, 4 H), 2.18–1.98 (m, 2 H), 1.78–1.67 (m, 3 H), 1.31 (d, J=6.6 Hz, 3 H). IR (KBr) 3270, 2960, 2942, 2912, 2830, 2821, 1743, 1682, 1596, 1390, 1273, 1199.

Analysis calculated for $C_{32}H_{36}N_2O_5$: C, 72.70; H, 6.86; N, 5.30. Found: C, 72.42; H, 6.65; N, 5.25.

In like manner, other phenol-ketones of the Preparation below are converted to:

2-(4-Benzyl-4-hydroxypiperidino)-1-(4-(4-morpholinomethyl)benzoyloxy)phenyl)-1-propanone; and 2-(4-(4-Chlorophenyl)-4-hydroxypiperidino)-1-(4-(morpholinomethyl)benzoyloxy)phenyl-1-propanone.

EXAMPLE 2

Racemic (1S*,2S*)- and (1R*,2S*)-2-(4-Hydroxy-4-phenylpiperidino)-1-(4-(4-(morpholinomethyl)benzoyloxy)phenyl)-1-propanol Sodium borohydride (0.39 g, 10.3 mmol) was partially dissolved in absolute ethanol (25 mL) and chilled to 0° C. and an ice cold ethanol solution (50 mL) of the title ketone product of the preceding Example (5.0 g, 9.46 mmol) was added over 2 minutes. The reaction was stirred at 0° C. overnight, and then it was quenched with glacial acetic acid (6 mL). The volatiles were distilled from the reaction mixture under vacuum while maintaining the pot temperature at or below 0° C. The residual material was flash chromatographed on silica gel (2×6 inches, ethyl acetate/hexane gradient elution). No product was obtained. Continued elution with a methanol/ethyl acetate gradient gave 2.90 g of the (S*,S*)-title product, which was recrystallized from ethanol to give 1.8 g of purified (S*,S*)-title product: m.p. 172°–173° C.; NMR (CDCl$_3$) 8.17 (d, J=8.3 Hz, 2 H), 7.56–7.25 (m, 9 H), 7.20 (d, J=8.5 Hz, 2 H), 4.33 (d, J=9.7 Hz, 1 H), 3.73 (t, J=4.6 Hz, 4 H), 3.59 (s, 2 H), 3.11 (dt, J=1.7, 11.6 Hz, 1 H), 2.76–2.59 (m, 4 H), 2.47 (t, J=4.5 Hz, 4 H), 2.31–2.07 (m, 3 H), 1.85 (br d, J=13.2 Hz, 3 H), 0.89 (d, J=6.7 Hz, 3 H); IR (KBr) 3452, 3245, 2970, 2930, 2893, 1730, 1273, 1262, 1194, 1114, 1075, 797, 758.

Analysis calculated for $C_{32}H_{38}N_2O_5$: C, 72.43; H, 7.22; N, 5.28. Found: C, 72.58; H, 6.95; N, 5.26.

Continued gradient elution with methanol/ethyl acetate gave 1.71 g of the (R*,S*)-title product as its acetate salt. It was further purified by recrystallization from ethanol/ether to give purified (R*,S*)-title product, 0.60 g of white powder: m.p. 164°–165° C.; NMR (DMSO-d$_6$) 8.10 (d, J=8.2 Hz, 2 H), 7.54 (d, J=8.2 Hz, 2 H), 7.45 (t, J=7.4 Hz, 4 H), 7.31 (t, J=7.5 Hz, 2 H), 7.21 (d, J=8.3 Hz, 3 H), 5.82 (br s, 4 H), 4.91 (d, J=4.1 Hz, 1 H), 3.59 (t, J=4.6 Hz, 4 H), 3.01–2.71 (m, 6 H), 2.50 (m, 4 H), 2.20–1.80 (m with s at 1.90 ppm, 5 H), 1.64–1.60 (m, 2 H), 1.01 (d, J=6.6 Hz, 3 H). IR (KBr) 2961, 2856, 2820, 1733, 1268, 1201, 1071.

Analysis calculated for $C_{32}H_{38}N_2O_5 \cdot C_2H_4O_2$: C, 69.13; H, 7.17; N, 4.74. Found: C, 70.39; H, 6.85; N, 4.86.

By the same method, the additional products of the preceding Example are converted to:

(1S*,2S*)- and (1R*,2S*)-2-(4-Benzyl-4-hydroxypiperidino)-1-(4-(4-(morpholinomethyl)benzoyloxy)phenyl-1-propanol; and (1S*,2S*)- and (1R*,2S*)-2-(4-(4-Chlorophenyl)-4-hydroxypiperidino)-1-(4-(4-(morpholinomethyl)benzoyloxy)phenyl-1-propanol.

EXAMPLE 3

1-(4-(4-Diethylaminomethyl)benzoyloxy)phenyl)-2-(4-hydroxy-4-phenylpiperidino)-1-propanone The coupling of 4-diethylaminomethylbenzoic acid with 1-(4-hydroxyphenyl)-2-(4-hydroxy-4-phenylpiperidino)-1-propanone was carried out essentially as in Example 1. The crude product was treated with ether and hexane with stirring and yielded the creamy white product in 73% yield in a state of purity suitable for the reduction step. A sample recrystallized from ether/hexane gave a white powder which had: m.p. 106°–107° C.; NMR (CDCl$_3$) 8.25 (d, J=8.8 Hz, 2 H), 8.15 (d, J=8.3 Hz, 2 H), 7.51 (t, J=7.2 Hz, 4 H), 7.38–7.22 (m, 5 H), 4.16 (q, J=6.7 Hz, 1 H), 3.66 (s, 2 H), 2.96–2.81 (m, 2 H), 2.71–2.67 (m, 2 H), 2.55 (q, J=7.1 Hz, 4 H), 2.22–2.00 (m, 3 H), 1.82–1.69 (m, 2 H), 1.35 (d, J=6.7 Hz, 3 H), 1.07 (t, J=7.1 Hz, 6 H). IR (KBr) 3452, 2969, 2935, 2833, 1738, 1681, 1264, 1198, 1164, 1064.

Analysis calculated for $C_{32}H_{38}N_2O_4$ C, 74.68; H, 7.44; N, 5.44. Found: C, 74.34; H, 7.28; N, 5.49.

In like manner, other phenol-ketones of the Preparation below are converted to:

1-(4-(4-(Diethylaminomethyl)benzoyloxy)phenyl)-2-(3-(phenylthio)-8-azabicyclo[3.2.1]oct-8-yl)-1-propanone;

2-(3-(4-Chlorophenylthio)-8-azabicyclo[3.2.1]oct-8-yl)-1-(4-(4-diethylaminomethyl)benzoyloxy)phenyl)-1-propanone;

1-(4-(4-(Diethylaminomethyl)benzoyloxy)phenyl)-2-(3-(2-thienylthio)-8-azabicyclo[3.2.1]oct-8-yl)-1-propanone;

2-(3-Benzyl-3-hydroxy-8-azabicyclo[3.2.1]oct-8-yl)-1-(4-(4-diethylaminoethyl)benzoyloxy)phenyl)-1-propanone; and 2-(3-Hydroxy-3-phenyl-8-azabicyclo[3.2.1]oct-8-yl)-1-(4-(4-diethylamtnoethyl)benzoyloxy)phenyl)-1-propanone.

EXAMPLE 4

Racemic (1S*,2S*)- and (1R*,2S*)-1-(4-Diethylaminomethyl)benzoyloxy)phenyl)-2-(4-hydroxy-4-phenylpiperidino)-1-propanol The title product from the preceding Example was reduced with sodium borohydride as in Example 2. Purification by silica gel chromatography and recrystallization gave first (1S*,1S*)-title product (0.28 g, 28%) which had: m.p. 174°–175° C. (ethanol); NMR (CDCl$_3$) 8.14 (d, J=8.2 Hz, 2 H), 7.50 (t, J=8.3 Hz, 4 H), 7.43–7.35 (m, 4 H), 7.27 (t, J=7.2 Hz, 1 H), 7.18 (d, J=8.5 Hz, 2 H), 4.31 (d, J=9.7 Hz, 1 H), 3.64 (s, 2 H), 3.08 (t, J=10.6 Hz, 1 H), 2.72–2.60 (m, 4 H), 2.53 (q, J=7.1 Hz, 4 H), 2.27–2.05 (m, 2 H), 1.92 (br s, 1 H), 1.82 (br d, J=13.2 Hz, 2 H), 1.05 (t, J=7.1 Hz, 6 H), 0.87 (d, J=6.6 Hz, 3 H); IR (KBr) 3399, 2973, 2947, 1727, 1610, 1271, 1258, 1202, 1078.

Analysis calculated for $C_{32}H_{40}N_2O$: C, 74.39; H, 7.80; N, 5.42. Found: C, 74.31; H, 7.76; N, 5.38.

The second product isolated was the (1R*,1S*)-title product, as its acetate salt (0.119 g, 11%) which had: m.p. 148°–150° C. (ethanol); NMR (CDCl$_3$) 8.14 (d, J=8.3 Hz, 2 H), 7.52–7.27 (m, 10 H), 7.18 (d, J=8.6 Hz, 2 H), 5.45 (d, J=2.4 Hz, 1 H), 3.69 (s, 2 H), 3.50 (br d, J=11.6 Hz, 1 H), 3.27–3.22 (m, 2 H), 3.12–3.03 (m, 2 H), 2.57 (q, J=7.1 Hz, 4 H), 2.50–2.39 (m, 2 H), 2.04 (s, 3 H), 1.87 (br t, J=13.6 Hz, 2 H), 1.10–1.05 (m, 9 H); IR (KBr) 3167, 2967, 2962, 1737, 1257, 1205, 1172, 1071.

Analysis calculated for $C_{32}H_{40}N_2O_4 \cdot C_2H_4O_2$: C, 70.81; H, 7.69; N, 4.86. Found: C, 70.72; H, 7.64; N, 4.82.

The HCl salt of the (1S*,2S*)-title product recrystallized from ethanol/ether had: m.p. 180°–184° C. Analysis calculated for $C_{32}H_{40}N_2O_4 \cdot 2HCl \cdot 0.5 H_2O$: C, 64.20; H, 7.24; N, 4.61. Found: C, 64.02; H, 7.29; N, 4.42.

By the same method the other products of the preceding Example are converted to:

(1S*,2S*)- and (1R*,2S*)-1-(4-(4-Diethylaminomethyl)benzoyloxy)phenyl)-2-(3-(phenylthio-8-azabicyclo[3.2.1]-oct-8-yl)-1-propanol;

(1S*,2S*)- and (1R*,2S*)-2-(3-(4-Chlorophenylthio)-8-azabicyclo[3.2.1]oct-8-yl)-1-(4-(4-diethylaminomethyl)benzoyloxy)phenyl-1-propanol;

(1S*,2S*)- and (1R*,2S*)-1-(4-(4-Diethylaminomethyl)benzoyloxy)phenyl)-2-(2-(thienylthio)-8-azabicyclo[3.2.1]oct-8-yl)-1-propanol;

(1S*,2S*)- and (1R*,2S*)-2-(3-Benzyl-3-hydroxy-8-azabicyclo[3.2.1]oct-8-yl)-1-(4-(4-diethylaminoethyl)benzoyloxy)phenyl)-1-propanol; and (1S*,2S*)- and (1R*,2S*)-2-(3-Hydroxy-3-phenyl-8-azabicyclo[3.2.1]oct-8-yl)-1-(4-(4-diethylaminoethyl)benzoyloxy)phenyl)-1-propanol.

EXAMPLES 5–10

Substituting an equivalent amount of benzoic acid or of the appropriately substituted benzoic acid for the 4-(morpholinomethyl)benzoic acid, the method of Example 1 was used to prepare the following additional compounds:
5. 2-(4-Hydroxy-4-phenylpiperidino)-1-(4-(4-((1,1-dimethylethyl)aminomethyl)benzoyloxy)phenyl)-1-propanone; m.p. 156° C. (hexane trituration, 47% yield). 6. 1-(4-(Benzoyloxy)phenyl)-2-(4-hydroxy-4-phenylpiperidino)-1-propanone. 7. 2-(4-Hydroxy-4-phenylpiperidino)-1-(4-(4-(piperidinomethyl)benzoyloxy)phenyl)-1-propanone. 8. 2-(4-Hydroxy-4-phenylpiperidino)-1-(4-(4-(2-methylpiperidinomethyl)benzoyloxy)phenyl)-1-propanone. 9. 2-(4-Hydroxy-4-phenylpiperidino)-1-(4-(4-(dimethylaminomethyl)benzoyloxy)phenyl-1-propanone.
10. 1-(4-(3-(Diethylaminomethyl)benzoyloxy)phenyl)-2-(4-hydroxy-4-phenylpiperidino)-1-propanone.

EXAMPLE 11

Racemic (1S*,2S*)-2-(4-Hydroxy-4-phenylpiperidino)-1-(4-(4-((1,1-dimethylethyl)aminomethyl)benzoyloxy)phenyl)-1-propanol Lithium aluminum hydride (0.08 g, 2.11 mmol) was slurried in dry tetrahydrofuran (12 mL) and chilled to −78° C. The ketone product of Example 5 (0.44 g, 0.86 mmol) was added neat all at once to this cold slurry followed by continued stirring at −78° C. for 1 hour. The mixture which had now become a gel was diluted with tetrahydrofuran (10 mL) and quenched with acetic acid (0.48 mL, 8.4 mmol). The solvent was removed at reduced pressure and the residue was flash chromatographed on silica gel (1×6 inches, packed in 30% ethyl acetate/hexane). Ethyl acetate/hexane gradient elution gave no product. Continued elution with 10% methanol/ethyl acetate yielded the product as an actate salt. This solid was suspended in ethyl acetate and vigorously shaken with saturated sodium bicarbonate. The phases were separated and the aqueous layer was extracted twice with ethyl acetate. The combined organic layer was dried over calcium sulfate and concentrated. The residue was recrystallized from methanol to afford 30 mg (6.7%) of the title product as a white solid; m.p. 195°–197° C.; NMR (CDCl₃) 8.15 (d, J=8.5 Hz, 2 H), 7.53 (t, J=7 Hz, 4 H), 7.48–7.24 (m, 5 H), 7.20 (d, J=8.5 Hz, 2 H), 4.34 (d, J=9.5 Hz, 1 H), 3.85 (s, 2 H), 3.13 (long range coupled t, J=10.5 Hz, 1 H), 2.86–2.61 (m, 4 H), 2.38–2.09 (sym m, 2 H), 1.88 (br d, J=13.5 Hz, 2 H), 1.38 (small impurity), 1.26 (s, 1 H), 0.90 (d, J=6.5 Hz, 3 H). One hydroxyl proton was not observed.

Analysis calculated for $C_{32}H_{40}N_2O_4$: C, 74.39; H, 7.80; N, 5.42. Found: C, 73.98; H, 7.80; N, 5.18.

EXAMPLES 12–16

Using the ketone reduction procedures of the prior Examples, the ketones of Examples 6–10 were converted to the following racemic compounds:

12a. (1S*,2S*)-1-(4-(Benzoyloxy)phenyl)-2-(4-hydroxy-4-phenylpiperidino)-1-propanol; 38% yield; m.p. 166° C. (from ethanol).

12b. (1R*,2S*)-1-(4-(Benzoyloxy)phenyl)-2-(4-hydroxy-4-phenylpiperidino)-1-propanol; 17% yield; m.p. 188°–191° C. (from ethanol).

13a. (1S*,2S*)-2-(4-Hydroxy-4-phenylpiperidino)-1-(4-(4-(piperidinomethyl)benzoyloxy)phenyl)-1-propanol; 29% yield; m.p. 175° C. (dec), (from ethyl acetate).

13b. (1R*,2S*)-2-(4-Hydroxy-4-phenylpiperidino)-1-(4-(4-(piperidinomethyl)benzoyloxy)phenyl)-1-propanol; 15% yield; m.p. 167° C. (dec), (from ethyl acetate).

14a. (1S*,2S*)-2-(4-Hydroxy-4-phenylpiperidino)-1-(4-(4-(2-methylpiperidinomethyl)benzoyloxy)phenyl)-1-propanol; 37% yield; m.p. 179° C. (dec), (from ethyl acetate).

14b. (1R*,2S*)-2-(4-Hydroxy-4-phenylpiperidino)-1-(4-(4-(2-methylpiperidinomethyl)benzoyloxy)phenyl)-1-propanol; 16% yield; m.p. 160° C. (dec), (from ethyl acetate).

15a. (1S*,2S*)-2-(4-Hydroxy-4-phenylpiperidino)-1-(4-(4-(2-dimethylaminomethyl)benzoyloxy)phenyl)-1-propanol; 7% yield; m.p. 195°–198° C. (dec), (from methanol).

15b. (1R*,2S*)-2-(4-Hydroxy-4-phenylpiperidino)-1-(4-(4-(2-dimethylaminomethyl)benzoyloxy)phenyl)-1-propanol; 26% yield; m.p. 162°–182° C. (dec), (from ethyl acetate).

16. (1S*,2S*)-1-(4-(3-(Diethylaminomethyl)benzoyloxy)phenyl)-2-(4-hydroxy-4-phenylpiperidino)-1-propanol; 14% yield; m.p. 119°–123° C. (from methylcyclohexane).

EXAMPLE 17

Racemic (1S*,2S*)-1-(4-(4-(Diethylaminomethyl)benzoyloxy)phenyl)-2-(4-hydroxy-4-phenylpiperidino)-1-propanol Carbonyl diimidizole (0.25 g, 1.54 mmol) and racemic (1S*,2S*)-1-(4-hydroxyphenyl)-2-(4-hydroxy-4-phenylpiperidino)-1-propanol hydrochloride (0.37 g, 1.52 mmol; Chenard, International Patent Application Publication No. WO 90/14088, Example 38 at page 42) in dry $CH_2Cl_2$ (10 ml) were stirred for 1 hour at ambient temperature. 4-(Diethylaminomethyl)benzoic acid (0.50 g, 1.53 mmol) was then added and the resulting mixture was stirred overnight. The reaction mixture was then washed with saturated $NaHCO_3$, $H_2O$ and brine, dried with $MgSO_4$ and concentrated to give a white solid (0.41 g) which ¹HNMR (CDCl₃) showed to be a mixture of the acid, desired monoester and undesired diesterified material. Purification by silica gel flash chromatography (1×6 inches, ethyl acetate/hexane gradient for elution) gave 100 mg of crude title product as a colorless oil. This material was recrystallized from ethanol to yield purified title product (33 mg, 4.2%) having properties identical with those of the (1S*, 2S*)-title product of Example 4.

By the same method, the enantiomeric (1S,2S)- and (1R,2R)-1-(4-hydroxyphenyl)-2-(4-hydroxy-4-phenylpiperidino)-1-propanols (WO 90/14088, Example 78 at page 47) are converted to the corresponding 4-(diethylaminomethyl)benzoate esters.

PREPARATION 1-(4-Hydroxyphenyl)-2-(4-hydroxy-4-phenylpiperidino)-1-propanone 1-(4-(Triisopropylsilyloxy)phenyl)-2-(4-hydroxy-4-phenylpiperidino)-1-propanone (International Application Publication Number: WO 90/14088, Example 36 at page 41; 22.0 g, 45.7 mmol) was dissolved in dry tetrahydrofuran (500 mL). Tetrabutylammonium fluoride (55 ml, 55 mmol, 1N in tetrahydrofuran) was added dropwise to the stirred solution over 3 minutes. After stirring for 1 hour, the reaction mixture was concentrated and the concentrate flash chromatographed on silica gel (3×6 inches). The column was gradiently eluted with ethyl acetate/hexane, then sequentially with 100% ethyl acetate, 1:9 methanol:ethyl acetate and finally with 1:5 methanol: ethyl acetate. Product-containing fractions were stripped to yield 16.7 g (100%) of title product as a light yellow solid which was triturated with hexane; m.p. 95°–97° C.; $^1$H-NMR (CDCl$_3$) delta (ppm) 8.08 (d, J=8.5 Hz, 2 H), 7.48 (d, J=8 Hz, 2 H), 7.34 (t, J=8 Hz, 2 H), 7.28–7.25 (m, 1 H partially obscured by CHCl$_3$ from NMR solvent), 6.89 (d, J=8.5 Hz, 2 H), 4.15 (q, J=7 Hz, 1 H), 3.0–2.65 (m, 4 H), 2.25–2.10 (m, 2 H), 1.85–1.77 (m, 2 H), 1.35 (d, J=7 Hz, 3 H).

By the same method, other triisopropylsilyl protected ketones of said WO 90/14088 were converted to unprotected ketones as follows:

2-(4-Benzyl-4-hydroxypiperidino)-1-(4-hydroxyphenyl)-1-propanone;

2-(4-(4-Chlorophenyl)-4-(hydroxypiperidino)-1-(4-hydroxyphenyl)-1-propanone;

1-(4-Hydroxyphenyl)-2-(3-(phenylthio)-8-azabicyclo [3.2.1]oct-8-yl)-1-propanone;

2-(3-(4-Chlorophenylthio)-8-azabicyclo[3.2.1]oct-8-yl)-1-(4-hydroxyphenyl)-1-propanone;

1-(4-Hydroxyphenyl)-2-(3-(2-thienylthio)-8-azabicyclo [3.2.1]oct-8-yl)-1-propanone;

2-(3-Benzyl-3-hydroxy-8-azabicyclo[3.2.1]oct-8-yl)-1-(4-hydroxyphenyl)-1-propanone; and 1-(4-Hydroxyphenyl)-2-(3-hydroxy-3-phenyl-8-azabicyclo[3.2.1]oct-8-yl)-1-propanone.

I claim:

1. A compound of the formula

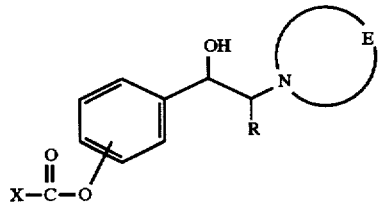

(II)

wherein

E is

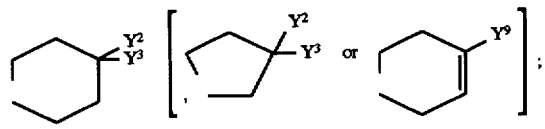

R is H, (C$_1$–C$_6$)alkyl, (C$_2$–C$_6$)alkenyl or (C$_2$–C$_6$)alkynyl;

X is phenyl or phenoxy;

Y$^2$ and Y$^3$ are taken together and are

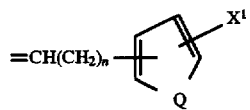

Y$^2$ and Y$^3$ are taken separately, and Y$^2$ is OH and Y$^3$ is

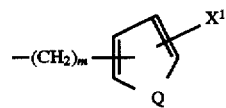

Y$^9$ is

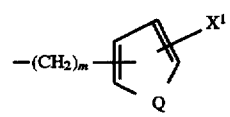

n is 0, 1, 2 or 3;

m is 0, 1, 2, 3 or 4;

Q is CH=CH; and

X$^1$ is hydrogen, (C$_1$–C$_3$)alkyl, (C$_1$–C$_3$)alkoxy or halo; or a pharmaceutically-acceptable acid addition salt thereof.

2. A compound of claim 1 wherein R is methyl having 1S*,2S* relative stereochemistry:

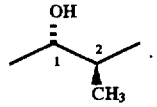

3. A pharmaceutical composition comprising a neuroprotective amount of a compound of claim 1 and a pharmaceutically-acceptable carrier.

4. A method of treating stroke, traumatic head injury or a CNS degenerative disease in a human in need of said treatment which comprises administering to said human a neuroprotective effective amount of a compound of claim 1.

5. A method of treating stroke in a human suffering from stroke or the symptoms thereof comprising administering to said human an effective amount of a compound of claim 1.

6. A method of treating traumatic head injury in a human suffering from traumatic head injury comprising administering to said human an amount of a compound of claim 1 which is effective in treating said traumatic brain injury.

7. A method of treating a CNS degenerative disease in a human suffering from a CNS degenerative disease comprising administering to said human an amount of a compound of claim 1 which is effective in treating said CNS degenerative disease.

* * * * *